United States Patent
Kanai et al.

(10) Patent No.: US 7,380,980 B2
(45) Date of Patent: Jun. 3, 2008

(54) DETECTOR FOR DETECTING STATE ON DETECTION SURFACE

(75) Inventors: Yoshiyuki Kanai, Tokyo (JP); Kazumasa Ibata, Tokyo (JP); Masaki Takechi, Tokyo (JP); Shingo Masumoto, Tokyo (JP); Yasuhiro Kajio, Tokyo (JP); Shigeki Shoji, Tokyo (JP); Ryu Akimoto, Tokyo (JP)

(73) Assignee: Yamatake Corporation, Tokyo (JP)

( * ) Notice: Subject to any disclaimer, the term of this patent is extended or adjusted under 35 U.S.C. 154(b) by 73 days.

(21) Appl. No.: 10/593,803

(22) PCT Filed: Mar. 16, 2005

(86) PCT No.: PCT/JP2005/004649

§ 371 (c)(1),
(2), (4) Date: Sep. 30, 2006

(87) PCT Pub. No.: WO2005/098404

PCT Pub. Date: Oct. 20, 2005

(65) Prior Publication Data

US 2007/0147466 A1 Jun. 28, 2007

(30) Foreign Application Priority Data

Mar. 30, 2004 (JP) .............................. 2004-101426

(51) Int. Cl.
*G01N 25/02* (2006.01)
*G01N 19/10* (2006.01)
*G01N 25/56* (2006.01)

(52) U.S. Cl. ........................... 374/19; 374/18; 374/27; 374/28; 73/29.02; 73/25.04

(58) Field of Classification Search .................. 374/19, 374/18, 27, 28
See application file for complete search history.

(56) References Cited

U.S. PATENT DOCUMENTS 3,528,278 A 9/1970 Sterling (Continued)

FOREIGN PATENT DOCUMENTS

JP 61-075235 A 4/1986

(Continued)

OTHER PUBLICATIONS

"Industrial Measurement Handbook", Asakura Publishing Co., Ltd., Sep. 30, 1976, p. 297.

*Primary Examiner*—Gail Verbitsky
*Assistant Examiner*—Mirellys Jagan
(74) *Attorney, Agent, or Firm*—Blakely, Sokoloff, Taylor & Zafman LLP

(57) ABSTRACT

The long-side surface of a triangular prism is a detection surface. The distal end portions of coaxial light-emitting/light-receiving optical fiber cables are joined to one short-side surface of the prism. A thermoelectric cooling element is mounted on the other short-side surface of the prism. A mirror is provided between the cooling surface of the thermoelectric cooling element and the short-side surface. When dew condensation occurs on the detection surface, part of light applied from an optical fiber on the light-emitting side onto the lower surface of the detection surface exits from the prism through the condensed dew. The specular reflection returns to the lower detection surface by a mirror surface and is specularly reflected again. The specular reflection then enters an optical fiber on the light-emitting side. Dew condensation on the detection surface is detected by a change in the intensity of light received through the optical fiber.

3 Claims, 12 Drawing Sheets

U.S. PATENT DOCUMENTS 4,924,084 A * 5/1990 Lask et al. ............. 250/227.25
5,022,045 A * 6/1991 Elliott ......................... 374/20
6,575,621 B1 * 6/2003 Zlochin ....................... 374/28

FOREIGN PATENT DOCUMENTS

| | | |
|---|---|---|
| JP | 62-163949 A | 7/1987 |
| JP | 63-165561 U | 10/1988 |
| JP | 01-010587 U | 3/1989 |
| JP | 05-002183 B | 1/1993 |
| JP | 07-104304 B | 11/1996 |
| JP | 2780045 B | 5/1998 |
| JP | 2002-529700 A | 9/2002 |

* cited by examiner

DETECTOR FOR DETECTING STATE ON DETECTION SURFACE

This is a non-provisional application claiming the benefit of International application number PCT/JP2005/004649, filed Mar. 16, 2005.

BACKGROUND OF THE INVENTION

The present invention relates to a detector for detecting a state on a detection surface to detect a state on the detection surface.

BACKGROUND ART

As a conventional humidity measurement method, a dew point detection method of detecting a dew point by lowering the temperature of a gas to be measured and measuring a temperature at which part of water vapor contained in the gas condenses is known. For example, reference 1 (industrial measurement handbook, Asakura Publishing Co., Ltd., Sep., 30, 1976, p. 297) discloses a chilled mirror dew point hygrometer which detects the dew point of moisture in a gas to be measured by chilling a mirror by using a refrigerant, freezer, electronic refrigerator, or the like, detecting a change in the intensity of reflected light on the chilled mirror surface, and measuring the temperature of the mirror surface at this point of time.

Such chilled mirror dew point hygrometers are categorized into two types according to the type of reflected light to be used. One type is based on a specular reflection detection scheme using specular reflection as disclosed in reference 2 (Japanese Patent Laid-Open No. 61-75235). The other type is based on a scattered light detection scheme using scattered light as disclosed in reference 3 (Japanese Patent Publication NO. 7-104304).

[Specular Reflection Detection Scheme]

FIG. 15 shows the main part of a conventional chilled mirror dew point hygrometer using the specular reflection detection scheme. A chilled mirror dew point hygrometer 101 comprises a chamber 1 in which a gas to be measured is caused to flow and a thermoelectric cooling element (Peltier element) 2 provided in the chamber 1. A bolt 4 is mounted on a cooling surface 2-1 of the thermoelectric cooling element 2 through a copper block 3, and a radiator fin 5 is mounted on a heating surface 2-2 of the thermoelectric cooling element 2. An upper surface 4-1 of the bolt 4 mounted on the copper block 3 is a mirror surface. A wire-wound resistance temperature detector (temperature detection element) 6 is embedded in a side portion of the copper block 3 (see FIG. 19). A light-emitting element 7 which obliquely applies light to the upper surface (mirror surface) 4-1 of the bolt 4 and a light-receiving element 8 which receives specular reflection of light applied from the light-emitting element 7 to the upper surface 4-1 are mounted in the upper portion of the chamber 1. A heat insulation material 40 is provided around the thermoelectric cooling element 2.

In the chilled mirror dew point hygrometer 101, the mirror surface 4-1 in the chamber 1 is exposed to the gas to be measured which is caused to flow into the chamber 1. If no dew condensation has occurred on the mirror surface 4-1, almost the entire amount of light emitted from the light-emitting element 7 is specularly reflected, and received by the light-receiving element 8. If, therefore, no dew condensation has occurred on the mirror surface 4-1, the reflected light received by the light-receiving element 8 has a high intensity.

As the temperature of the cooling surface 2-1 of the thermoelectric cooling element 2 is lowered by increasing the current to the thermoelectric cooling element 2, water vapor contained in a gas to be measured condenses into water on the mirror surface 4-1, and part of light emitted from the light-emitting element 7 is absorbed and reflected diffusely by the molecules of the water. As a consequence, the intensity of the reflected light (specular reflection) received by the light-receiving element 8 decreases. Detecting a change in specular reflection on the mirror surface 4-1 makes it possible to know a change in state on the mirror surface 4-1, i.e., the adhesion of moisture (water droplets) onto the mirror surface 4-1. In addition, the dew point of moisture in the gas to be measured can be known by indirectly measuring the temperature of the 4-chamber 1 using the temperature detection element 6.

[Scattered Light Detection Scheme]

FIG. 16 shows the main part of a conventional chilled mirror dew point hygrometer using the scattered light detection scheme. A chilled mirror dew point hygrometer 102 has almost the same arrangement as that of the chilled mirror dew point hygrometer 101 using the specular reflection detection scheme except for the mount position of the light-receiving element 8. In the chilled mirror dew point hygrometer 102, the light-receiving element 8 is placed at a position to receive scattered light instead of a position to receive specular reflection of light applied from the light-emitting element 7 to the mirror surface 4-1.

In the chilled mirror dew point hygrometer 102, the mirror surface 4-1 is exposed to a gas to be measured which is caused to flow into the chamber 1. If no dew condensation has occurred on the mirror surface 4-1, almost the entire amount of light emitted from the light-emitting element 7 is specularly reflected, and the amount of light received by the light-receiving element 8 is very small. If no dew condensation has occurred on the mirror surface 4-1, the reflected light received by the light-receiving element 8 has a low intensity.

As the temperature of the cooling surface 2-1 of the thermoelectric cooling element 2 is lowered by increasing the current to the thermoelectric cooling element 2, water vapor contained in the gas to be measured condenses into water on the mirror surface 4-1. Part of light emitted from the light-emitting element 7 is absorbed and reflected diffusely by the molecules of the water. As a consequence, the intensity of light (scattered light) reflected diffusely by the light-receiving element 8 increases. Detecting a change in scattered light on the mirror surface 4-1 makes it possible to know a change in state on the mirror surface 4-1, i.e., the adhesion of moisture (water droplets) on the mirror surface 4-1. In addition, the dew point of moisture in the gas to be measured can be known by indirectly measuring the temperature of the mirror surface 4-1 using the temperature detection element 6.

The above hygrometer is described by taking, as an example, the detection of dew condensation (moisture) which occurs on the mirror surface 4-1. However, the same arrangement can detect frost formation (moisture) which occurs on the mirror surface 4-1.

With the arrangement shown in FIGS. 17 and 18, i.e., the arrangement in which the thermoelectric cooling element 2, the temperature detection element 6, and the like are omitted, only a mirror 9 is provided in the chamber 1, and an opening portion is formed in the upper surface of the chamber 1, this detector can also be used as a detector for detecting a state on a mirror surface (weather meter). In a weather meter 103 or 104, when rain, snow, or the like is introduced into the chamber 1 and adheres to the mirror surface 9-1 of the mirror 9, the adhesion is detected on the basis of the intensity of reflected light received by the light-receiving element 8.

SUMMARY OF THE INVENTION

However, in the above conventional chilled mirror dew point hygrometer 101 or 102 or weather meter 103 or 104, since the optical system which includes the light-emitting element, the light-receiving element, and the like to detect dew condensation or frost formation is provided above the mirror surface (detection surface), the optical system interferes with the cleaning of the mirror surface and makes it difficult to clean it. In addition, the adhesion of dust or the like to the mirror surface will decrease the intensity of reflected light, resulting in an increase in measurement error.

The present invention has been made to solve such problems, and has as its object to provide a detector for detecting a state on a detection surface and a moisture detection device which allow easy cleaning of the detection surface and reduce the influence of dust.

Means of Solution to the Problem

In order to achieve the above object, according to the present invention, there is provided a detector for detecting a state on a detection surface, comprising a prism which includes a first surface as a detection surface, light-emitting means for applying light to the detection surface through an interior of the prism, light-receiving means for receiving reflected light of light applied from the light-emitting means to the detection surface, and state detection means for detecting a state on the detection surface on the basis of the reflected light received by the light-receiving means.

According to the present invention, the first surface of the prism, e.g., the surface with a long side (long-side surface) of a triangular prism, serves as a detection surface, and light is applied to the detection surface through the interior of the prism. The reflected light of the light applied to this detection surface, i.e., the light applied to the lower surface of the detection surface, is received, and a state (e.g., the adhesion of rain or snow, dew condensation, or frost formation) on the detection surface is detected on the basis of the received reflected light.

In the present invention, when rain or snow adheres to the detection surface of the prism, part of the light applied from the light-emitting means to the lower surface of the detection surface exits from the prism through the rain or snow adhering to the lower surface. Consequently, the specular reflection of the light applied to the lower surface of the detection surface is reduced. The specular reflection of the light applied to the lower surface of this detection surface is directly received by the light-receiving means, is returned to the lower surface of the detection surface of the mirror to be specularly reflected thereby again, and is received by the light-receiving means, thereby allowing the detection of the adhesion of rain or snow to the detection surface in accordance with a change in the intensity of this received light. Letting the mirror totally reflect the light, in particular, makes the light pass through the lower surface of the detection surface twice, thereby increasing the degree of attenuation of the light.

Effects of the Invention

According to the present invention, light is applied to the detection surface (the lower surface of the detection surface) through the interior of the prism, and a state on the detection surface is detected on the basis of the specular reflection of the light applied to the detection surface of the detection surface. Therefore, there is no need to place an optical system above the detection surface. This makes it possible to facilitate cleaning of the detection surface. In addition, even if dust or the like adheres to the detection surface, hardly any light exits from the prism through the dust, thereby making this detector unlikely to be influenced by the dust.

DETAILED DESCRIPTION OF THE INVENTION

The present invention will be described in detail with reference to the accompanying drawings.

First Embodiment

Chilled Mirror Dew Point Hygrometer (Reflection Scheme)

Figure 1:
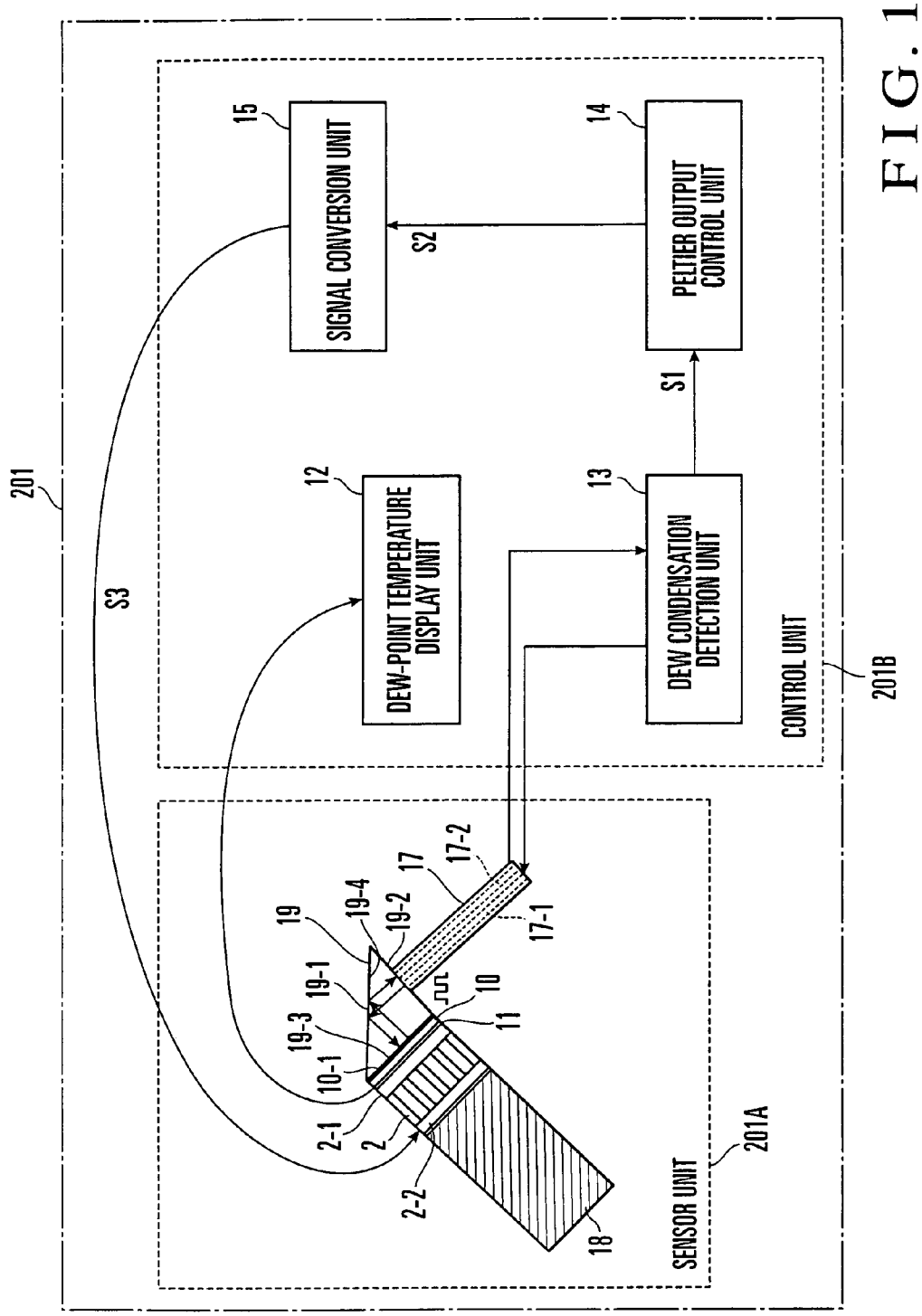
FIG. 1 is a schematic view of the arrangement of a chilled mirror dew point hygrometer showing an embodiment (first embodiment) of a detector for detecting a state on a detection surface according to the present invention.

FIG. 1 is a schematic view showing the arrangement of a chilled mirror dew point hygrometer showing an embodiment of a detector for detecting a state on a detection surface according to the present invention. A chilled mirror dew point hygrometer 201 includes a sensor unit 201A and a control unit 201B.

The sensor unit 201A comprises a triangular prism (to be simply referred to as a prism hereinafter) 19. A long-side surface (first surface) 19-1 of the prism 19 serves as a detection surface. An end face of a tube (or cable) 17 made of stainless steel is joined to one short-side surface (second surface) 19-2 bordered on the detection surface 19-1 of the prism 19. A thermoelectric cooling element (Peltier element) 2 is mounted on the other short-side surface (third surface) 19-3 bordered on the detection surface 19-1 of the prism 19 through a mirror 10. The mirror 10 comprises, for example, a mirror coating. A thin-film resistance temperature detector (temperature detection element) 11 made of platinum is formed on the joint surface between the mirror 10 and a cooling surface 2-1 of the thermoelectric cooling element 2. A columnar heat sink 18 is joined to a heating surface 2-2 of the thermoelectric cooling element 2.

Figure 2A:
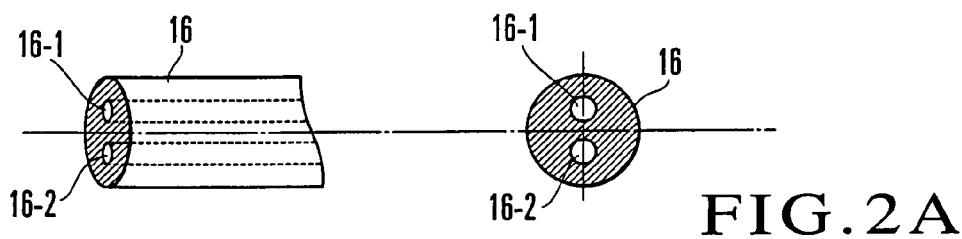
FIG. 2A is a view exemplifying the arrangement in which an optical fiber on the light-emitting side and an optical fiber on the light-receiving side are coaxially provided in one tube.
Figure 2B:
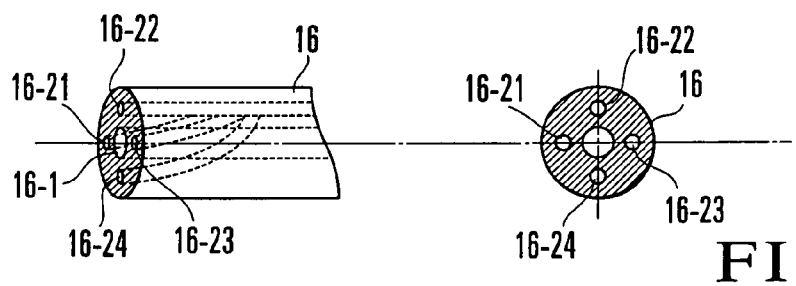
FIG. 2B is a view exemplifying the arrangement in which an optical fiber on the light-emitting side and optical fibers on the light-receiving side are coaxially provided in one tube.
Figure 2C:
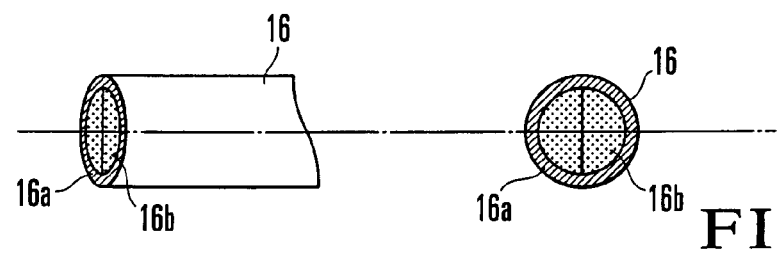
FIG. 2C is a view exemplifying the arrangement in which an optical fiber on the light-emitting side and an optical fiber on the light-receiving side are coaxially provided in one tube.
Figure 2D:
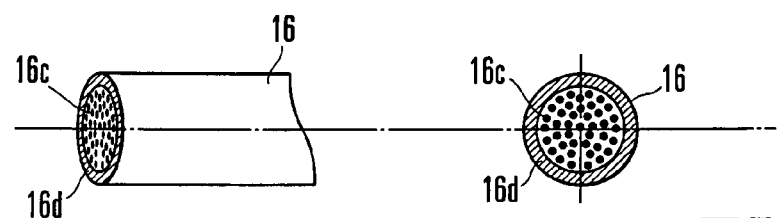
FIG. 2D is a view exemplifying the arrangement in which optical fibers on the light-emitting side and optical fibers on the light-receiving side are coaxially provided in one tube.
Figure 2E:
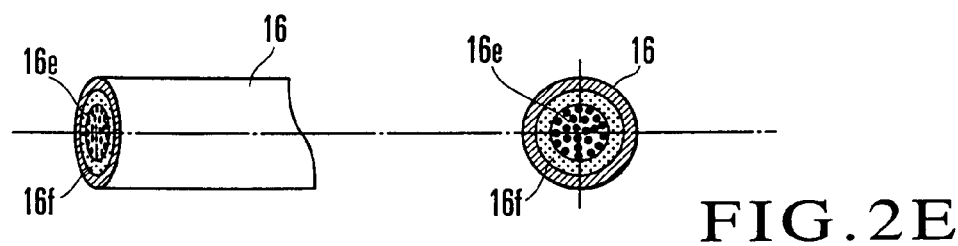
FIG. 2E is a view exemplifying the arrangement in which an optical fiber on the light-emitting side and optical fibers on the light-receiving side are coaxially provided in one tube.

In this embodiment, as the tube 17, one of various types of tubes 16 accommodating optical fibers in various forms like those shown in FIGS. 2A to 2E can be used. Referring to FIG. 2A, the tube 16 coaxially accommodates an optical fiber 16-1 on the light-emitting side and an optical fiber 16-2 on the light-receiving side. Referring to FIG. 2B, the tube 16 coaxially accommodates an optical fiber 16-1 on the light-emitting side (or the light-receiving side) and optical fibers 16-21 to 16-24 on the light-receiving side (or the light-emitting side). Referring to FIG. 2C, in the tube 16, the left half portion is formed into an optical fiber 16a on the light-emitting side, and the right half portion is formed into an optical fiber 16b on the light-receiving side. Referring to FIG. 2D, the tube 16 accommodates optical fibers 16c on the light-emitting side and optical fibers 16d on the light-receiving side in a mixed state. Referring to FIG. 2E, in the tube 16, the central portion accommodates optical fibers 16e on the light-emitting side (or the light-receiving side), and an optical fiber 16f on the light-receiving side (or the light-emitting side) is placed around the optical fibers 16e.

The chilled mirror dew point hygrometer 201 shown in FIG. 1 uses the tube 16 shown in FIG. 2A as the tube 17, which accommodates an optical fiber 17-1 on the light-emitting side and an optical fiber 17-2 on the light-receiving side. The distal end portions (the light-emitting and light-receiving portions) of the optical fiber 17-1 on the light-emitting side and optical fiber 17-2 on the light-receiving side are joined to the second surface 19-2 of the prism 19 and directed to the lower surface (lower detection surface) 19-4 of the prism 19. As a consequence, the applying direction (optical axis) of light from the optical fiber 17-1 and the receiving direction (optical axis) of light in the optical fiber 17-2 are made parallel to each other, and are placed adjacent to each other at the same tilt angle.

In this embodiment, the second and third surfaces 19-3 and 19-3 of the prism 19 define an angle of 90°, and the detection surface (first surface) 19-1 and the second surface 19-2 and the detection surface (first surface) 19-1 and the third surface 19-3 both define an angle of 45°. Therefore, the tilt angles of the optical fibers 17-1 and 17-2 with respect to the lower detection surface 19-4 are set to 45°.

The control unit 201B comprises a dew-point temperature display unit 12, dew condensation detection unit 13, Peltier output control unit 14, and signal conversion unit 15. The dew-point temperature display unit 12 displays the temperature of the prism 19 which is detected by the temperature detection element 11. The dew condensation detection unit 13 applies pulse light from the distal end portion of the optical fiber 7-1 to the lower detection surface 19-4 of the prism 19 at a predetermined period, and obtains, as the intensity of reflected pulse light, the difference between the upper and lower limit values of the reflected pulse light which is received through the optical fiber 17-2 as described above. The dew condensation detection unit 13 sends a signal S1 corresponding to the intensity of the reflected pulse light to the Peltier output control unit 14. Upon receiving the signal S1 from the dew condensation detection unit 13, the Peltier output control unit 14 compares the intensity of the reflected pulse light with a predetermined threshold. If the intensity of the reflected pulse light exceeds the threshold, a control signal S2 for increasing the current to the thermoelectric cooling element 2 in accordance with the value of the signal S1 is output to the signal conversion unit 15. If the intensity of the reflected pulse light is lower than the threshold, the signal S2 for decreasing the current to the thermoelectric cooling element 2 in accordance with the value of the signal S1 is output to the signal conversion unit 15. The signal conversion unit 15 supplies, to the thermoelectric cooling element 2, a current S3 designated by the control signal S2 from the Peltier output control unit 14.

Figure 3A:
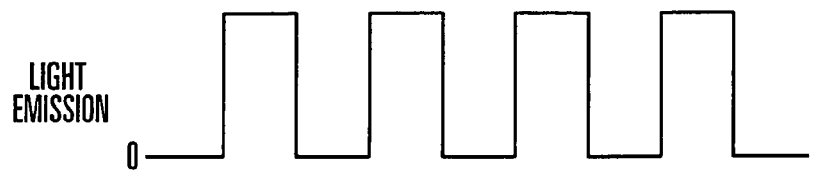
FIG. 3A is a waveform chart of pulse light applied to the mirror surface.

In the chilled mirror dew point hygrometer 201, the sensor unit 201A is placed in a gas to be measured. The dew condensation detection unit 13 also applies pulse light from the distal end portion of the optical fiber 17-1 to the lower detection surface 19-4 of the prism 19 at a predetermined period (see FIG. 3A). The detection surface 19-1 is exposed to the gas to be measured. If, therefore, no dew condensation has occurred on the detection surface 19-1, the entire amount of pulse light applied from the distal end portion of the optical fiber 17-1 is specularly reflected (totally reflected) by the lower detection surface 19-4 and reaches a mirror surface 10-1 placed at the third surface 19-3 of the prism 19. The pulse light is then totally reflected by the mirror surface 10-1, and returns to the lower detection surface 19-4. The pulse light is totally reflected by the lower detection surface 19-4, and almost 100% of the reflected light enters the optical fiber 17-2. If, therefore, no dew condensation has occurred on the detection surface 19-1, the reflected pulse light received through the optical fiber 17-2 has a high intensity.

The dew condensation detection unit 13 obtains the difference between the upper and lower limit values of the reflected pulse light received through the optical fiber 17-2 as the intensity of the reflected pulse light, and sends the signal S1 corresponding to the intensity of the reflected pulse light to the Peltier output control unit 14. In this case, since the intensity of the reflected pulse light is high and exceeds the threshold, the Peltier output control unit 14 sends, to the signal conversion unit 15, the control signal S2 for increasing the current to the thermoelectric cooling element 2. This increases the current S3 from the signal conversion unit 15 to the thermoelectric cooling element 2 and lowers the temperature of the cooling surface 2-1 of the thermoelectric cooling element 2.

Figure 4:
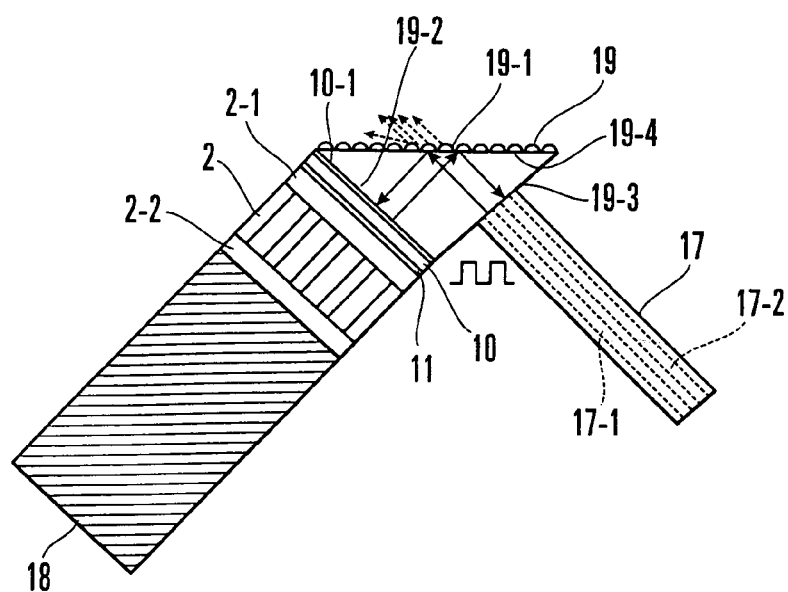
FIG. 4 is a view showing how part of light applied to the lower detection surface exits from the prism through condensed dew produced on the detection surface in the first embodiment.

As the temperature of the cooling surface 2-1 of the thermoelectric cooling element 2, i.e., the temperature of the prism 19, lowers, water vapor contained in the gas to be measured condenses on the detection surface 19-1 of the prism 19, and part of light applied from the optical fiber 17-1 to the lower detection surface 19-4 exits from the prism 19 through the condensed dew (see FIG. 4). For this reason, the incident light is not totally reflected by the lower detection surface 19-4, and the amount of light specularly reflected by the lower detection surface 19-4 decreases. This specular reflection returns to the lower detection surface 19-4 by the mirror surface 10-1 and specularly reflected again by the lower detection surface 19-4 to enter the optical fiber 17-2. In this embodiment, in particular, light is totally reflected by the mirror surface 10-1 to pass through the lower detection surface 19-4 twice, resulting in an increase in the degree of attenuation of light. This decreases the intensity of the reflected pulse light received through the optical fiber 17-2.

Figure 3B:
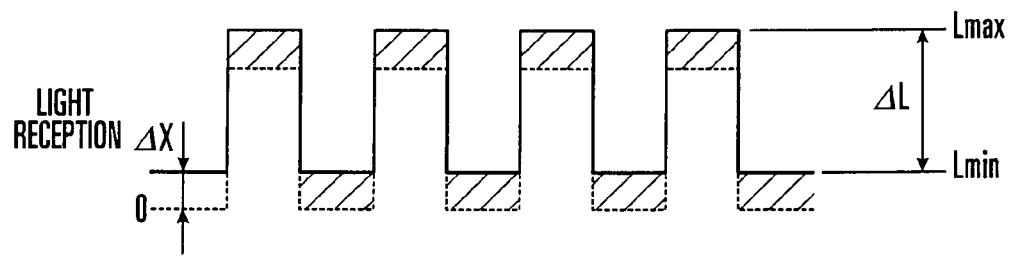
FIG. 3B is a waveform chart of reflected pulse light received from the mirror surface.

The dew condensation detection unit 13 obtains the difference between the upper and lower limit values of each pulse of received reflected pulse light, and sets it as the intensity of the reflected pulse light. That is, as shown in FIG. 3B, the dew condensation detection unit 13 obtains a difference $\Delta L$ between an upper limit value Lmax and a lower limit value Lmin of one pulse of reflected pulse light, and sets the difference $\Delta L$ as the intensity of reflected pulse light. With this processing by the dew condensation detection unit 13, disturbance light $\Delta X$ contained in the reflected pulse light is removed to prevent an operation error due to the disturbance light. The processing scheme of preventing an operation error due to disturbance light by using the pulse light detected by the dew condensation detection unit 13 will be called a pulse modulation scheme. This processing makes it possible to eliminate a chamber from the sensor unit 201A in the chilled mirror dew point hygrometer 201.

If the intensity of reflected pulse light received through the optical fiber 17-2 decreases below the threshold, the Peltier output control unit 14 sends, to the signal conversion unit 15, the control signal S2 for decreasing the current to the thermoelectric cooling element 2. This suppresses a drop in the temperature of the cooling surface 2-1 of the thermoelectric cooling element 2 and the occurrence of dew condensation. With this suppression of dew condensation, the intensity of reflected pulse light received through the optical fiber 17-2 increases. If the intensity exceeds the threshold, the Peltier output control unit 14 sends, to the signal conversion unit 15, the control signal S2 for increasing the current to the thermoelectric cooling element 2. Repeating this operation adjusts the temperature of the cooling surface 2-1 of the thermoelectric cooling element 2 so as to make the intensity of the reflected pulse light received through the optical fiber 17-2 become almost equal to the threshold. The adjusted temperature, i.e., the temperature (dew-point temperature) at which the dew condensation which has occurred on the detection surface 19-1 has reached an equilibrium state is displayed as a dew-point temperature on the dew-point temperature display unit 12.

In the chilled mirror dew point hygrometer 201, light is applied to the lower detection surface 19-4 through the interior of the prism 19, and dew condensation which has occurred on the detection surface 19-1 is detected on the basis of the specular reflection of the light applied to the detection surface 19-4. Therefore, there is no need to place an optical system above the detection surface 19-1. This facilitates cleaning of the detection surface 19-1. In addition, even if dust or the like adheres to the detection surface 19-1, hardly any light exits from the prism 19 through the dust, and total reflection by the lower detection surface 19-4 is continued, thereby making this detector unlikely to be influenced by the dust.

Furthermore, mounting the optical fiber 17-1 on the light-emitting side and the optical fiber 17-2 on the light-receiving side on one portion in the chilled mirror dew point hygrometer 201 contributes to a reduction in the size of the sensor unit 201A. Since the tube 17 accommodates the optical fiber 17-1 on the light-emitting side and the optical fiber 17-2 on the light-receiving side, there is no need to perform positioning between the optical fiber 17-1 on the light-emitting side the optical fiber 17-2 on the light-receiving side, improving workability at the time of assembly.

In addition, in the chilled mirror dew point hygrometer 201, a chamber can be omitted from the sensor unit 201A, and a suction pump and suction tube which are used to draw a gas to be measured into the chamber, an exhaust tube, a flow meter, and the like can be omitted, and hence the number of parts can be reduced. This makes it possible to further reduce the size of the sensor unit 201A, improving assembly, and achieving a reduction in cost. Furthermore, since there is no need to mount a suction pump and suction tube, an exhaust tube, a flow meter, and the like, the hygrometer can be easily placed in an atmosphere to be measured. Moreover, since there is no need to mount a suction pump and suction tube, an exhaust tube, a flow meter, and the like in the sensor unit 201A, and the hygrometer comprises the two components, i.e., the sensor unit 201A and the control unit 201B, the hygrometer can be easily carried.

Figure 7:
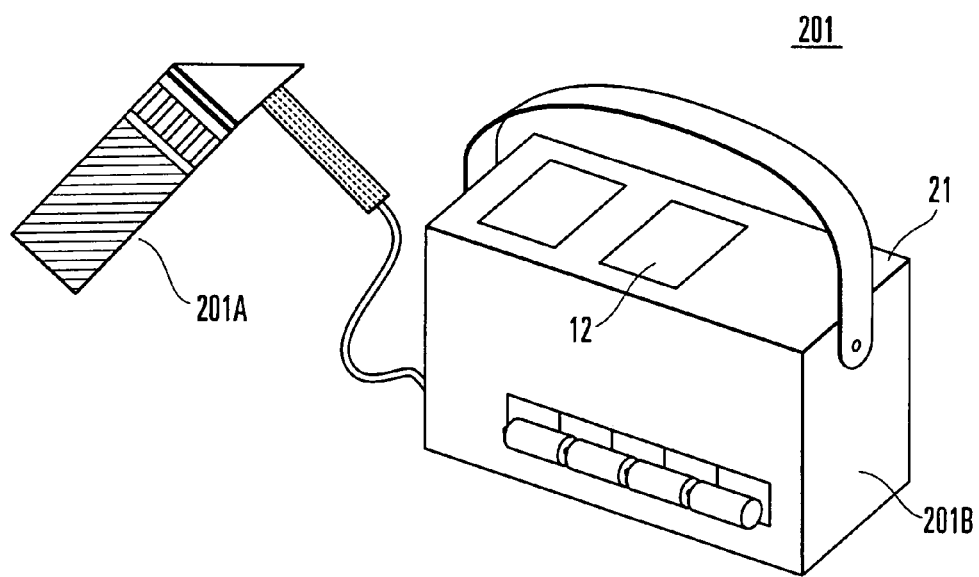
FIG. 7 is a view showing the arrangement of a chilled mirror dew point hygrometer in which a control unit is housed in a control box.

FIG. 7 shows the arrangement of the chilled mirror dew point hygrometer 201 having the control unit 201B housed in a control box 21. In the control box 21, a battery is used as a power supply for the housed control unit 201B. When a user carries the set of the control box 21 and the sensor unit 201A to a site and places the sensor unit 201A in an atmosphere to be measured, measurement can be quickly started. In this case, the control box 21 and the sensor unit 201A are separate parts. However, the sensor unit 201A may be provided in the control box 21 and they may be integrated into one part.

In addition, since the chilled mirror dew point hygrometer 201 has the temperature detection element 11 provided on the joint surface between the cooling surface 2-1 of the thermoelectric cooling element 2 and the mirror 10, the temperature of the prism 19 can be accurately measured with good responsiveness and little heat resistance. This improves the measurement accuracy of a dew-point temperature and responsiveness. Furthermore, the mirror 10 and the third surface 19-3 of the prism 19 can be integrated to achieve a reduction in size, thereby improving assembility. This makes it possible to decrease the number of parts and the cost. The mirror 10 may be joined to the cooling surface 2-1 of the thermoelectric cooling element 2. This makes it possible to integrate the thermoelectric cooling element 2 and the mirror 10 into an integral form, thereby achieving a reduction in size.

The chilled mirror dew point hygrometer 201 shown in FIG. 1 uses the tube 17 accommodating the optical fiber 17-1 on the light-emitting side and the optical fiber 17-2 on the light-receiving side in the sensor unit 201A. However, a light-emitting diode and a photocoupler may be provided instead of the optical fiber 17-1 on the light-emitting side and the optical fiber 17-2 on the light-receiving side, respectively. In addition, light applied/received by the optical fibers may be focused by a lens or the like to be collimated.

Second Embodiment

Chilled Mirror Dew Point Hygrometer
(Transmission Scheme)

Figure 5:
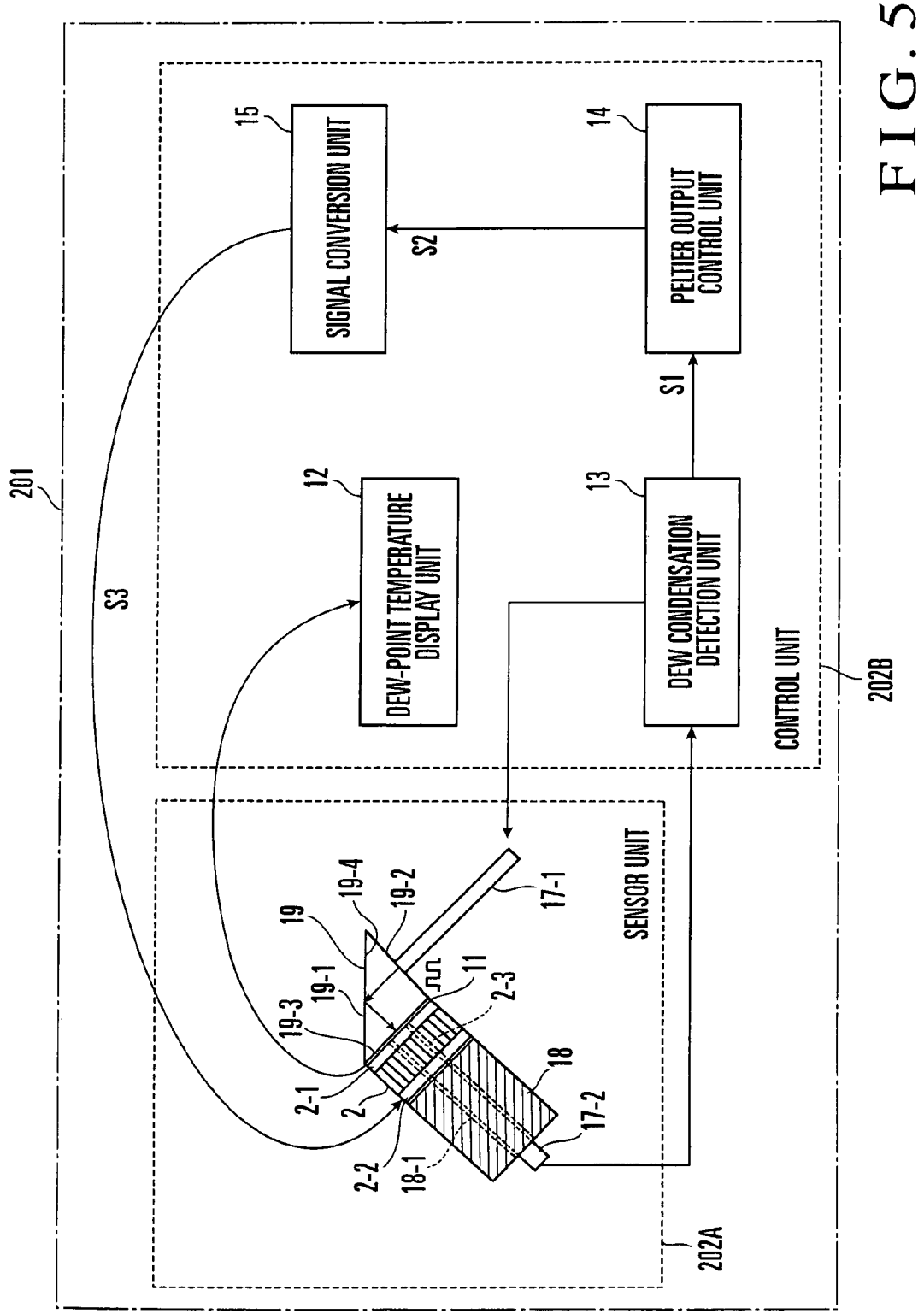
FIG. 5 is a schematic view showing the arrangement of a chilled mirror dew point hygrometer showing another embodiment (second embodiment) of the detector for detecting a state on the detection surface according to the present invention.

FIG. 5 is a schematic view showing the arrangement of a chilled mirror dew point hygrometer showing another embodiment of the moisture detection device according to the present invention. In a chilled mirror dew point hygrometer 202, an optical fiber 17-1 on the light-emitting side and an optical fiber 17-2 on the light-receiving side are separately provided on the second surface 19-2 side and third surface 19-3 side of a prism 19 instead of being provided coaxially. That is, the distal end face (light-emitting portion) of the optical fiber 17-1 on the light-emitting side is joined to the second surface 19-2 of the prism 19, and the distal end face (light-receiving portion) of the optical fiber 17-2 on the light-receiving side is joined to the third surface 19-3 of the prism 19. A thermoelectric cooling element 2 has a hollow portion in its central portion. A heat sink 18 has a hollow portion 18-1 in its central portion. The optical fiber 17-2 extends through the hollow portions 2-3 and 18-1. Note that this embodiment does not use the mirror 10 like that shown in FIG. 1, and has a temperature detection element 11 located on the joint surface between the third surface 19-3 of the prism 19 and a cooling surface 2-1 of the thermoelectric cooling element 2.

In the chilled mirror dew point hygrometer 202, a sensor unit 202A is placed in a gas to be measured. The dew condensation detection unit 13 applies pulse light from the distal end portion of the optical fiber 17-1 to a lower detection surface 19-4 of the prism 19 at a predetermined period. The detection surface 19-1 is exposed to the gas to be measured. If, therefore, no dew condensation has occurred on the detection surface 19-1, the entire amount of the pulse light applied from the distal end portion of the optical fiber 17-1 is specularly reflected (totally reflected) by the lower detection surface 19-4, and almost 100% of the reflected light enters the optical fiber 17-2 located at the third surface 19-3 of the prism 19. If, therefore, no dew condensation has occurred on the detection surface 19-1, the reflected pulse light received through the optical fiber 17-2 has a high intensity.

A dew condensation detection unit 13 obtains the difference between the upper and lower limit values of the reflected pulse light received through the optical fiber 17-2 as the intensity of the reflected pulse light, and sends a signal S1 corresponding to the intensity of the reflected pulse light to a Peltier output control unit 14. In this case, since the intensity of the reflected pulse light is high and exceeds the threshold, the Peltier output control unit 14 sends, to a signal conversion unit 15, a control signal S2 for increasing the current to the thermoelectric cooling element 2. This increases a current S3 from the signal conversion unit 15 to the thermoelectric cooling element 2 and lowers the temperature of the cooling surface 2-1 of the thermoelectric cooling element 2.

Figure 6:
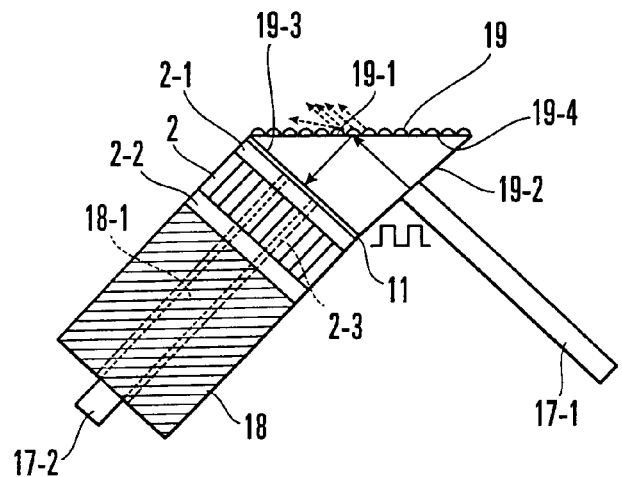
FIG. 6 is a view showing how part of light applied to the lower detection surface exits from the prism through condensed dew produced on the detection surface.

As the temperature of the cooling surface 2-1 of the thermoelectric cooling element 2, i.e., the temperature of the prism 19, lowers, water vapor contained in the gas to be measured condenses on a detection surface 19-1 of the prism 19, and part of light applied from the optical fiber 17-1 to the lower detection surface 19-4 exits from the prism 19 through the condensed dew (see FIG. 6). For this reason, the incident light is not totally reflected by the lower detection surface 19-4, and the amount of light specularly reflected by the lower detection surface 19-4 decreases. This specular reflection enters the optical fiber 17-2. This decreases the intensity of the reflected pulse light received through the optical fiber 17-2.

If the intensity of reflected pulse light received through the optical fiber 17-2 decreases below the threshold, the Peltier output control unit 14 sends, to the signal conversion unit 15, the control signal S2 for decreasing the current to the thermoelectric cooling element 2. This suppresses a drop in the temperature of the cooling surface 2-1 of the thermoelectric cooling element 2 and the occurrence of dew condensation. With this suppression of dew condensation, the intensity of reflected pulse light received through the optical fiber 17-2 increases. If the intensity exceeds the threshold, the Peltier output control unit 14 sends, to the signal conversion unit 15, the control signal S2 for increasing the current to the thermoelectric cooling element 2. Repeating this operation adjusts the temperature of the cooling surface 2-1 of the thermoelectric cooling element 2 so as to make the intensity of the reflected pulse light received through the optical fiber 17-2 become almost equal to the threshold. The adjusted temperature, i.e., the temperature (dew-point temperature) at which the dew condensation which has occurred on the detection surface 19-1 has reached an equilibrium state is displayed as a dew-point temperature on the dew-point temperature display unit 12.

In the chilled mirror dew point hygrometer 202, light is applied to the lower detection surface 19-4 through the interior of the prism 19, and dew condensation which has occurred on the detection surface 19-1 is detected on the basis of the specular reflection of the light applied to the detection surface 19-4. Therefore, there is no need to place an optical system above the detection surface 19-1. This facilitates cleaning of the detection surface 19-1. In addition, even if dust or the like adheres to the detection surface 19-1, hardly any light exits from the prism 19 through the dust, and total reflection by the lower detection surface 19-4 continues, thereby making this detector unlikely to be influenced by the dust.

Figure 8:
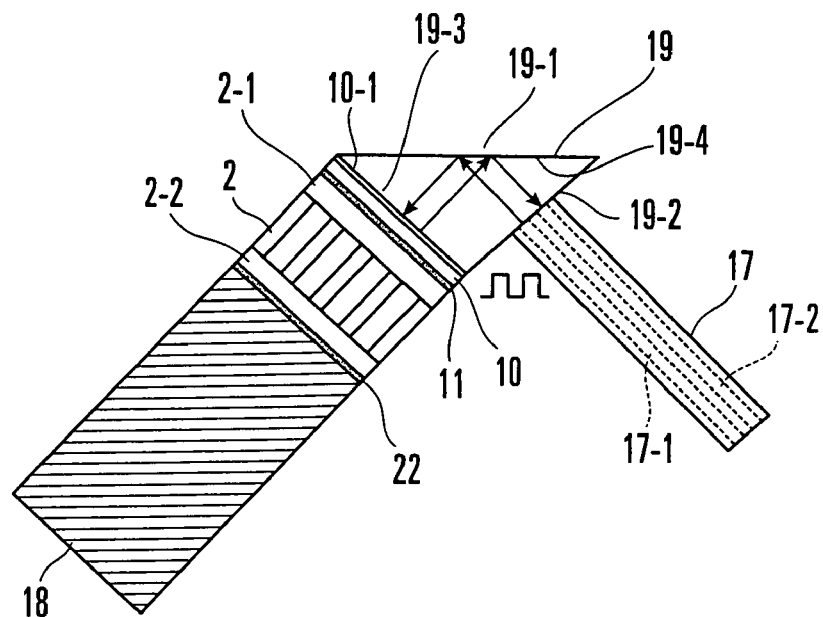
FIG. 8 is a view showing a modification of a sensor unit of the chilled mirror dew point hygrometer according to the first embodiment which includes a temperature detection element at the joint surface between the heating surface of a thermoelectric cooling element and a heat sink.
Figure 9:
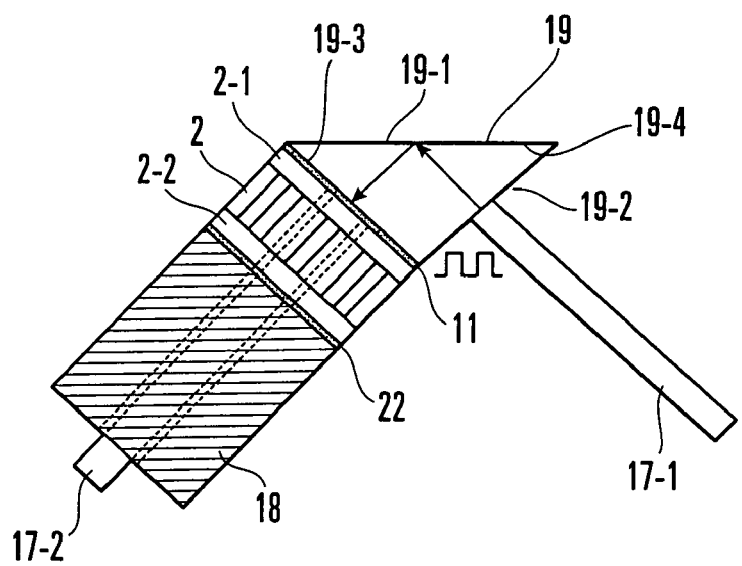
FIG. 9 is a view showing a modification of a sensor unit of the chilled mirror dew point hygrometer according to the second embodiment which includes a temperature detection element at the joint surface between the heating surface of a thermoelectric cooling element and a heat sink.

Furthermore, according to the first and second embodiments described above, the temperature of the prism 19 is detected only by providing the temperature detection element 11 at the joint surface between the cooling surface 2-1 of the thermoelectric cooling element 2 and the mirror 10. As shown in FIGS. 8 and 9, however, providing a temperature detection element 22 at the joint surface between a heating surface 2-2 of the thermoelectric cooling element 2 and the heat sink 18 makes it possible to measure the temperature of the heat sink 18 with high accuracy and responsiveness. In addition, the cooling efficiency for the prism 19 can be improved by, for example, interrupting or limiting the current to the thermoelectric cooling element 2 when the temperature of the heat sink 18 reaches a certain temperature.

Third Embodiment

Weather Meter (Reflection Scheme)

Figure 10:
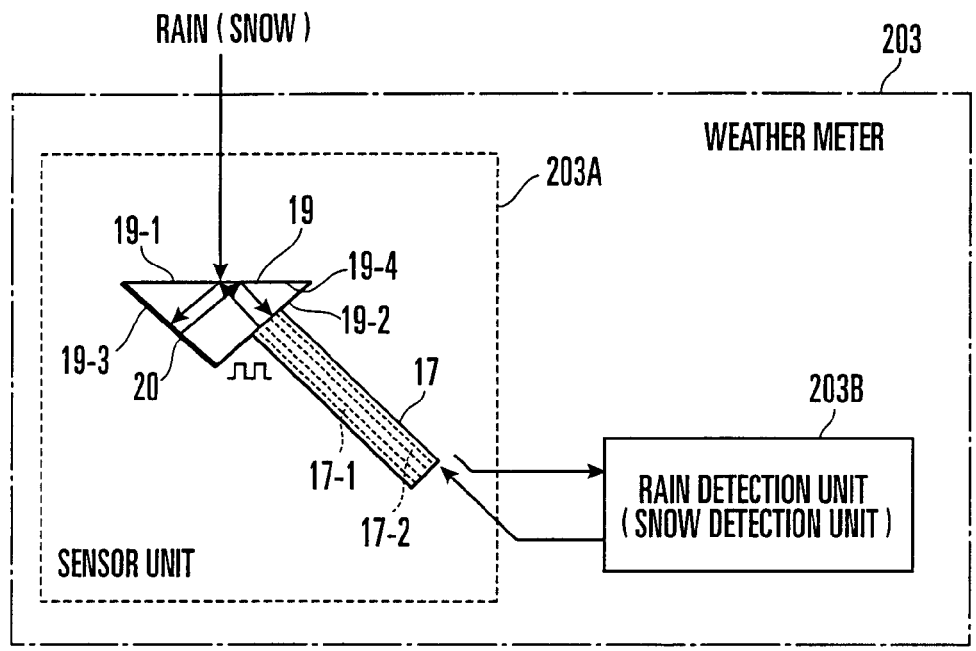
FIG. 10 is a schematic view showing the arrangement of a weather meter showing another embodiment (third embodiment) of the detector for detecting a state on the detection surface according to the present invention.

FIG. 10 is a schematic view showing the arrangement of a weather meter showing another embodiment of the detector for detecting a state on the detection surface according to the present invention. A weather meter 203 includes a sensor unit 203A and a rain detection unit 203B. The sensor unit 203A comprises only a prism 19, with the distal end portion of a tube 17 being joined to a second surface 19-2 of the prism 19 as in the first embodiment. Note that in this embodiment, a third surface 19-3 of the prism 19 is provided with a mirror coat 20.

In the weather meter 203, the rain detection unit 203B applies pulse light from the distal end portion of an optical fiber 17-1 to a lower detection surface 19-4 of the prism 19 at a predetermined period, and obtains the difference between the upper and lower limit values of reflected pulse light received through an optical fiber 17-2 as the intensity of the reflected pulse light. The rain detection unit 203B then compares the intensity of this reflected pulse light with a predetermined threshold. If the intensity of the reflected pulse light is lower than the threshold, the rain detection unit 203B determines that rain has begun to fall (rain has adhered to a detection surface 19-1).

Fourth Embodiment

Weather Meter (Transmitted Light Scheme)

Figure 11:
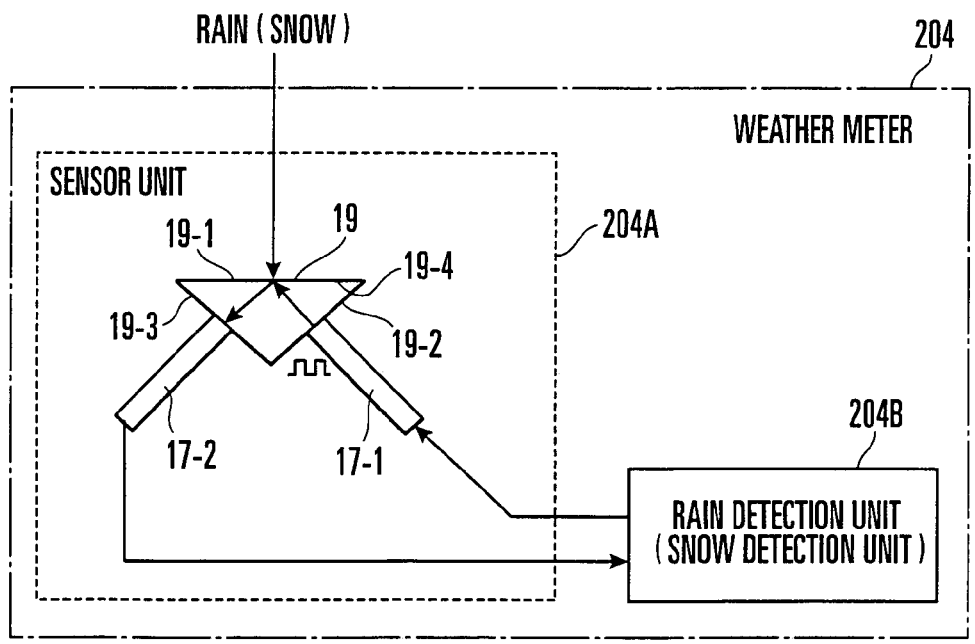
FIG. 11 is a schematic view showing the arrangement of a weather meter showing another embodiment (fourth embodiment) of the detector for detecting a state on the detection surface according to the present invention.

FIG. 11 is a schematic view showing the arrangement of a weather meter showing another embodiment of the detector for detecting a state on the detection surface according to the present invention. A weather meter 204 includes a sensor unit 204A and a rain detection unit 204B. The sensor unit 204A comprises only a prism 19, with a distal end portion of an optical fiber 17-1 being joined to a second surface 19-2 of the prism 19 and an optical fiber 17-2 on the light-receiving side being joined to a third surface 19-3 of the prism 19 as in the second embodiment.

In the weather meter 204, the rain detection unit 204B applies pulse light from the distal end portion of the optical fiber 17-1 to a lower detection surface 19-4 of the prism 19 at a predetermined period, and obtains the difference between the upper and lower limit values of reflected pulse light received through an optical fiber 17-2 as the intensity of the reflected pulse light. The rain detection unit 204B compares the intensity of the reflected pulse light with a predetermined threshold. If the intensity of the reflected pulse light decreases below the threshold, the rain detection unit 204B determines that rain has begun to fall (rain has adhered to a detection surface 9-1).

Fifth Embodiment

Chilled Mirror Dew Point Hygrometer

Figure 12:
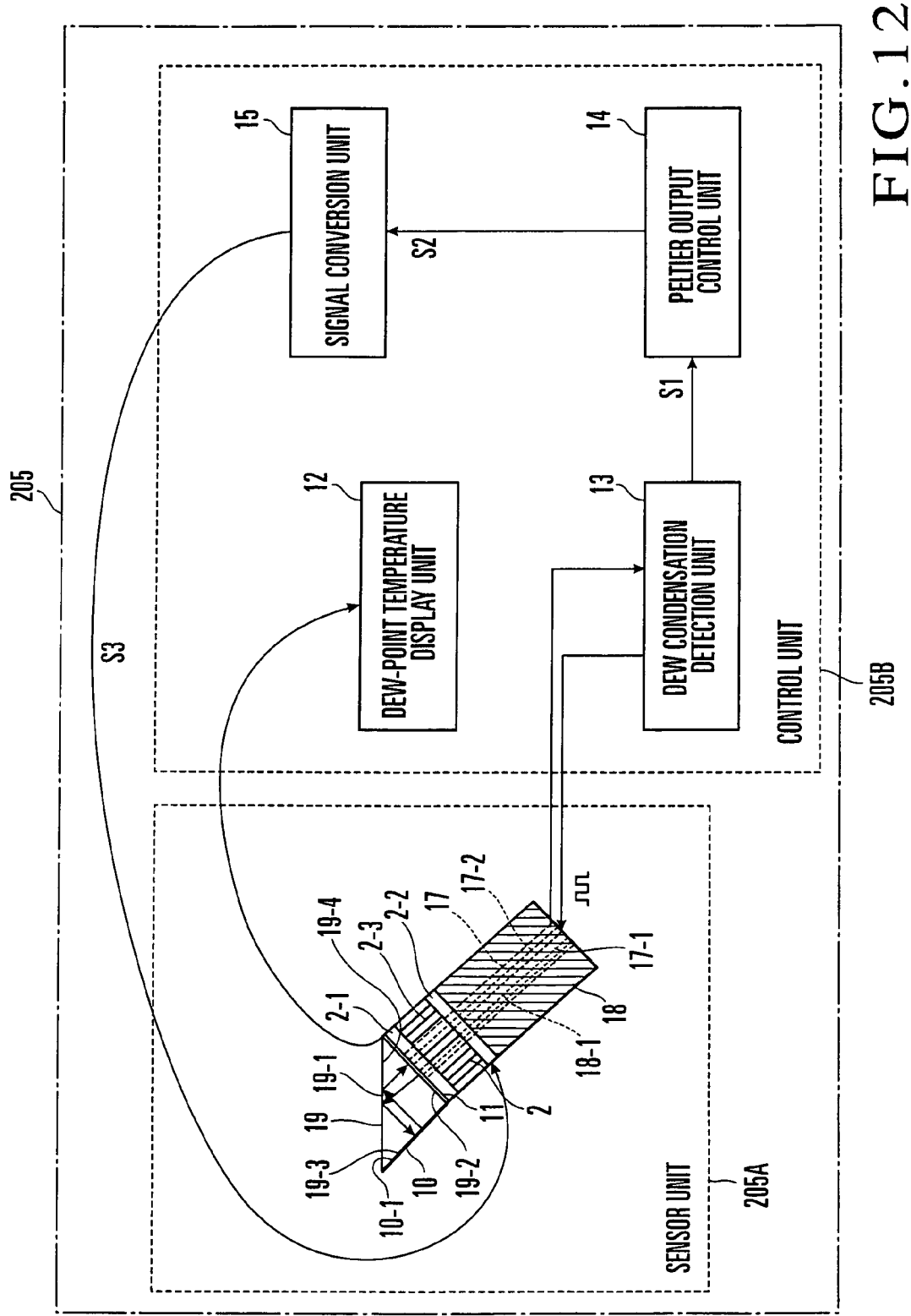
FIG. 12 is a schematic view showing the arrangement of a weather meter showing another embodiment (fifth embodiment) of the detector for detecting a state on the detection surface according to the present invention.

FIG. 12 is a schematic view showing the arrangement of a chilled mirror dew point hygrometer showing another embodiment of the detector for detecting a state on the detection surface according to the present invention. A chilled mirror dew point hygrometer 205 includes a control unit 205, sensor unit 205A, and control unit 205B.

The sensor unit 205A comprises a triangular prism 19. A long-side surface (first surface) 19-1 of the prism 19 serves as a detection surface. A thermoelectric cooling element (Peltier element) 2 is provided at one short-side surface (second surface) 19-2 bordered on a detection surface 19-1 of the prism 19. A mirror 10 is formed on the other short-side (third surface) 19-3 bordered on the detection surface 19-1 of the prism 19 by mirror coating.

The thermoelectric cooling element 2 comprises a cooling surface 2-1 on the second surface 19-2 side of the prism 19. A thin-film resistance temperature detector (temperature detection element) 11 made of platinum is formed on the joint surface between the cooling surface 2-1 of the thermoelectric cooling element 2 and the second surface 19-2 of the prism 19. A columnar heat sink (heat dissipation member) 18 is joined to a heating surface 2-2 of the thermoelectric cooling element 2.

In addition, the thermoelectric cooling element 2 has a hollow portion 2-3 in its central portion, and the heat sink 18 has a hollow portion 18-1 in its central portion. A tube 17 made of stainless still extends through the hollow portions 2-3 and 18-1, and the distal end face of the tube 17 is joined to the second surface 19-2 of the prism 19. Note that in order to bring the distal end face of the tube 17 into contact with the second surface 19-2 of the prism 19, the temperature detection element 11 is patterned to detour the corresponding portion.

This embodiment uses a tube 16 of the type shown in FIG. 2A as the tube 17, which accommodates an optical fiber 17-1 on the light-emitting side and an optical fiber 17-2 on the light-receiving side. The distal end portions (the light-emitting and light-receiving portions) of the optical fiber 17-1 on the light-emitting side and optical fiber 17-2 on the light-receiving side are joined to the second surface 19-2 of the prism 19 and directed to a lower surface (lower detection surface) 19-4 of the prism 19. As a consequence, the applying direction (optical axis) of light from the optical fiber 17-1 and the receiving direction (optical axis) of light in the optical fiber 17-2 are made parallel to each other, and are placed adjacent to each other at the same tilt angle.

In this embodiment, the second and third surfaces 19-2 and 19-3 of the prism 19 define an angle of 90°, and the detection surface (first surface) 19-1 and the second surface 19-2 and the detection surface (first surface) 19-1 and the third surface 19-3 both define an angle of 45°. Therefore, the tilt angles of the optical fibers 17-1 and 17-2 with respect to the lower detection surface 19-4 are set to 45°.

The control unit 205B comprises a dew-point temperature display unit 12, dew condensation detection unit 13, Peltier output control unit 14, and signal conversion unit 15. The dew-point temperature display unit 12 displays the temperature of the prism 19 which is detected by the temperature detection element 11. The dew condensation detection unit 13 applies pulse light from the distal end portion of the optical fiber 7-1 to the lower detection surface 19-4 of the prism 19 at a predetermined period, and obtains, as the intensity of reflected pulse light, the difference between the upper and lower limit values of the reflected pulse light which is received through the optical fiber 17-2 as will be described above. The dew condensation detection unit 13 sends a signal S1 corresponding to the intensity of the reflected pulse light to the Peltier output control unit 14. Upon receiving the signal S1 from the dew condensation detection unit 13, the Peltier output control unit 14 compares the intensity of the reflected pulse light with a predetermined threshold. If the intensity of the reflected pulse light exceeds the threshold, a control signal S2 for increasing the current to the thermoelectric cooling element 2 in accordance with the value of the signal S1 is output to the signal conversion unit 15. If the intensity of the reflected pulse light is lower than the threshold, the signal S2 for decreasing the current to the thermoelectric cooling element 2 in accordance with the value of the signal S1 is output to the signal conversion unit 15. The signal conversion unit 15 supplies a current S3 designated by the control signal S2 from the Peltier output control unit 14 to the thermoelectric cooling element 2.

In the chilled mirror dew point hygrometer 205, the sensor unit 205A is placed in a gas to be measured. The dew condensation detection unit 13 applies pulse light from the distal end portion of the optical fiber 17-1 to the lower detection surface 19-4 of the prism 19 at a predetermined period (see FIG. 3A). The detection surface 19-1 is exposed to the gas to be measured. If, therefore, no dew condensation has occurred on the detection surface 19-1, the entire amount of the pulse light applied from the distal end portion of the optical fiber 17-1 is specularly reflected (totally reflected) by the lower detection surface 19-4, and reaches a mirror surface 10-1 of the mirror 10 placed at the third surface 19-3 of the prism 19. The pulse light is then totally reflected by the mirror surface 10-1, and returns to the lower detection surface 19-4. The pulse light is totally reflected by the lower detection surface 19-4, and almost 100% of the reflected light enters the optical fiber 17-2. If, therefore, no dew condensation has occurred on the detection surface 19-1, the reflected pulse light received through the optical fiber 17-2 has a high intensity.

The dew condensation detection unit 13 obtains the difference between the upper and lower limit values of the reflected pulse light received through the optical fiber 17-2 as the intensity of the reflected pulse light, and sends the signal S1 corresponding to the intensity of the reflected pulse light to the Peltier output control unit 14. In this case, since the intensity of the reflected pulse light is high and exceeds the threshold, the Peltier output control unit 14 sends, to a signal conversion unit 15, the control signal S2 for increasing the current to the thermoelectric cooling element 2. This increases a current S3 from the signal conversion unit 15 to the thermoelectric cooling element 2 and lowers the temperature of the cooling surface 2-1 of the thermoelectric cooling element 2.

Figure 13:
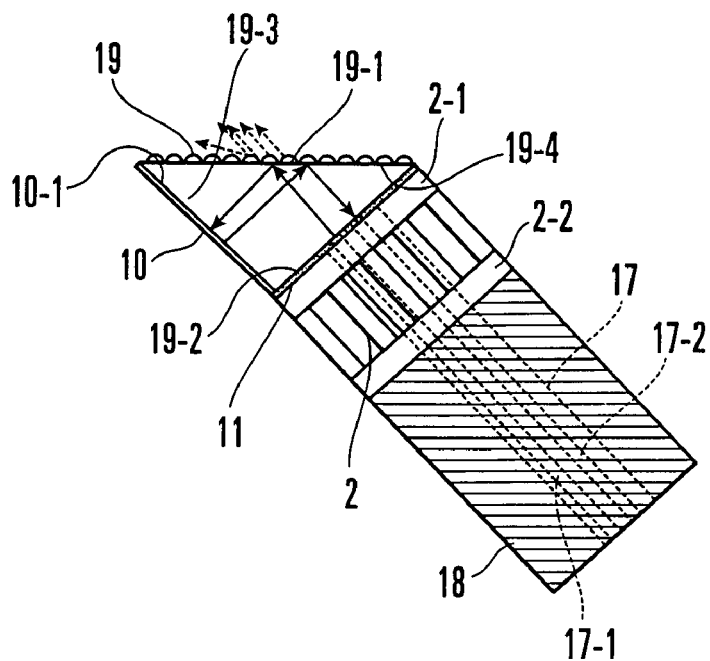
FIG. 13 is a view showing how part of light applied to the lower detection surface exits from the prism through condensed dew produced on the detection surface in the fifth embodiment.

As the temperature of the cooling surface 2-1 of the thermoelectric cooling element 2, i.e., the temperature of the prism 19, lowers, water vapor contained in the gas to be measured condenses on a detection surface 19-1 of the prism 19, and part of light applied from the optical fiber 17-1 to the lower detection surface 19-4 exits from the prism 19 through the condensed dew (see FIG. 13). For this reason, the incident light is not totally reflected by the lower detection surface 19-4, and the amount of light specularly reflected by the lower detection surface 19-4 decreases. This specular reflection returns to the lower detection surface 19-4 by the mirror surface 10-1 and is specularly reflected again by the lower detection surface 19-4 to enter the optical fiber 17-2. In this embodiment, in particular, light is totally reflected by the mirror surface 10-1 to pass through the lower detection surface 19-4 twice, resulting in an increase in the degree of attenuation of light. This decreases the intensity of the reflected pulse light received through the optical fiber 17-2.

The dew condensation detection unit 13 obtains the difference between the upper and lower limit values of each pulse of received reflected pulse light, and sets it as the intensity of the reflected pulse light. That is, as shown in FIG. 3B, the dew condensation detection unit 13 obtains a difference ΔL between an upper limit value Lmax and a lower limit value Lmin of one pulse of reflected pulse light, and sets the difference ΔL as the intensity of reflected pulse light. With this processing by the dew condensation detection unit 13, disturbance light ΔX contained in the reflected pulse light is removed to prevent an operation error due to the disturbance light. The processing scheme of preventing an operation error due to disturbance light by using the pulse light detected by the dew condensation detection unit 13 will be called a pulse modulation scheme. This processing makes it possible to eliminate a chamber from the sensor unit 205A in the chilled mirror dew point hygrometer 205.

If the intensity of reflected pulse light received through the optical fiber 17-2 decreases below the threshold, the Peltier output control unit 14 sends, to the signal conversion unit 15, the control signal S2 for decreasing the current to the thermoelectric cooling element 2. This suppresses a drop in the temperature of the cooling surface 2-1 of the thermoelectric cooling element 2 and the occurrence of dew condensation. With this suppression of dew condensation, the intensity of reflected pulse light received through the optical fiber 17-2 increases. If the intensity exceeds the threshold, the Peltier output control unit 14 sends, to the signal conversion unit 15, the control signal S2 for increasing the current to the thermoelectric cooling element 2. Repeating this operation adjusts the temperature of the cooling surface 2-1 of the thermoelectric cooling element 2 so as to make the intensity of the reflected pulse light received through the optical fiber 17-2 become almost equal to the threshold. The adjusted temperature, i.e., the temperature (dew-point temperature) at which the dew condensation which has occurred on the detection surface 19-1 has reached an equilibrium state is displayed as a dew-point temperature on the dew-point temperature display unit 12.

In the chilled mirror dew point hygrometer 205, light is applied to the lower detection surface 19-4 through the interior of the prism 19, and dew condensation which has occurred on the detection surface 19-1 is detected on the basis of the specular reflection of the light applied to the detection surface 19-4. Therefore, there is no need to place an optical system above the detection surface 19-1. This makes it possible to achieve a reduction in size and facilitate cleaning of the detection surface 19-1. In addition, even if dust or the like adheres to the detection surface 19-1, hardly any light exits from the prism 19 through the dust, and total reflection by the lower detection surface 19-4 is continued, thereby making this hygrometer unlikely to be influenced by the dust.

In addition, in the chilled mirror dew point hygrometer 205, the thermoelectric cooling element 2 is provided on the second surface 19-2 of the prism 19 which serves as the incident surface of light from the optical fiber 17-1 and the exit surface of light to the optical fiber 17-2. That is, the thermoelectric cooling element 2 is provided on the second surface 19-2 of the prism 19 at which the optical fibers 17-1 and 17-2 are located. This can further reduce the size of the chilled mirror dew point hygrometer as compared with the case wherein the thermoelectric cooling element 2 is provided on the third surface 19-3 of the prism 19 (the arrangement of the first embodiment (FIG. 1)).

In the first embodiment, since the thermoelectric cooling element 2 and the heat sink 18 are provided on the third surface 19-3 of the prism 19 through the mirror 10, parts are provided on the two short-side surfaces of the prism 19, resulting in an increase in size. In contrast to this, in the fifth embodiment, since the thermoelectric cooling element 2, the heat sink 18, and the optical fibers 17-1 and 17-2 are placed on the second surface 19-2 side of the prism 19, no components are placed on the third surface 19-3 side of the prism 19, resulting in a reduction in size. Furthermore, in the arrangement of the fifth embodiment, since the optical fiber 17-1 on the light-emitting side and the optical fiber 17-2 on the light-receiving side are placed in the hollow portions of the thermoelectric cooling element 2 and heat sink 18, a further reduction in size can be achieved.

Figure 14:
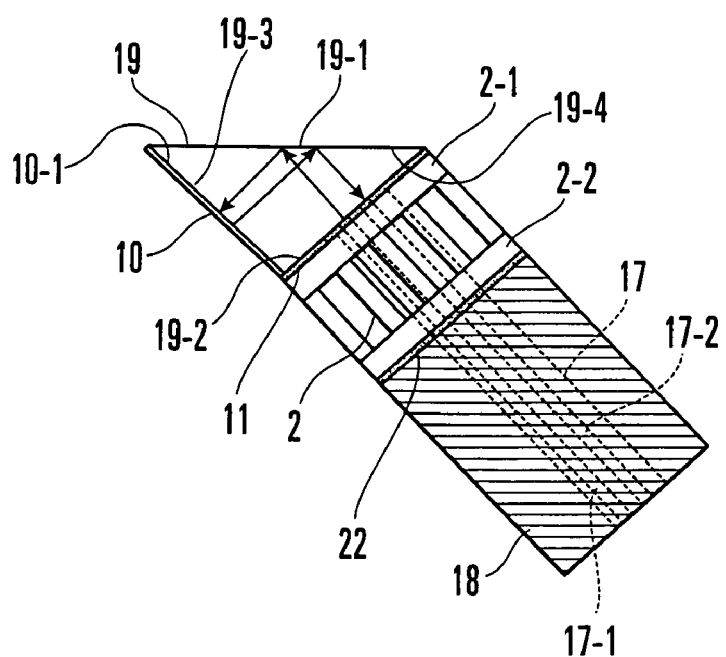
FIG. 14 is a view showing a modification of a sensor unit of the chilled mirror dew point hygrometer which includes a temperature detection element at the joint surface between the heating surface of a thermoelectric cooling element and a heat sink.
Figure 15:
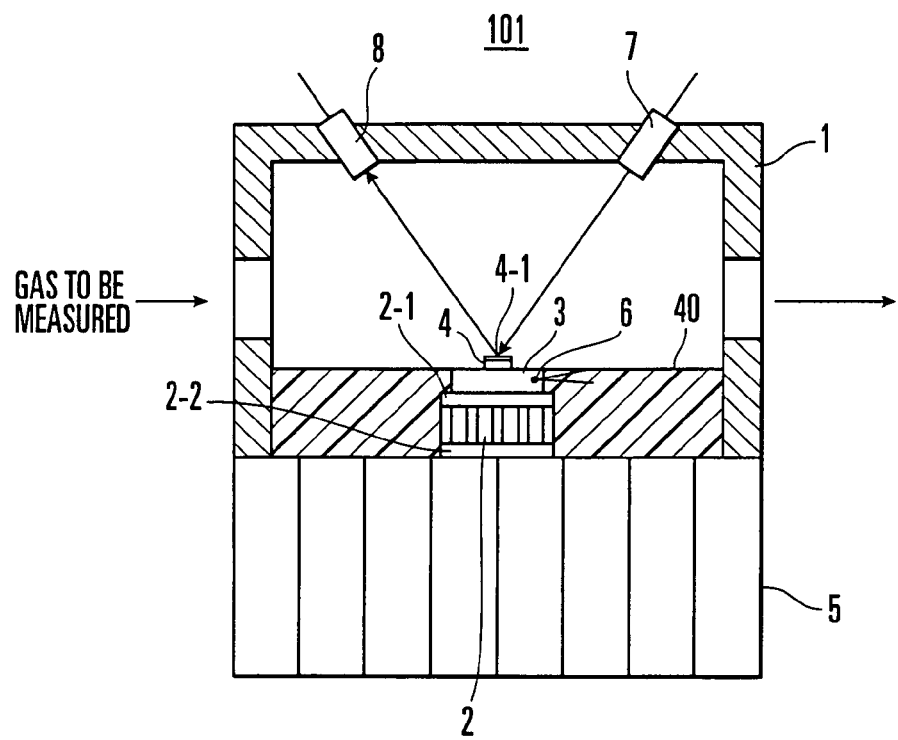
FIG. 15 is a view showing the main part of a conventional chilled mirror dew point hygrometer using the specular reflection detection scheme.
Figure 16:
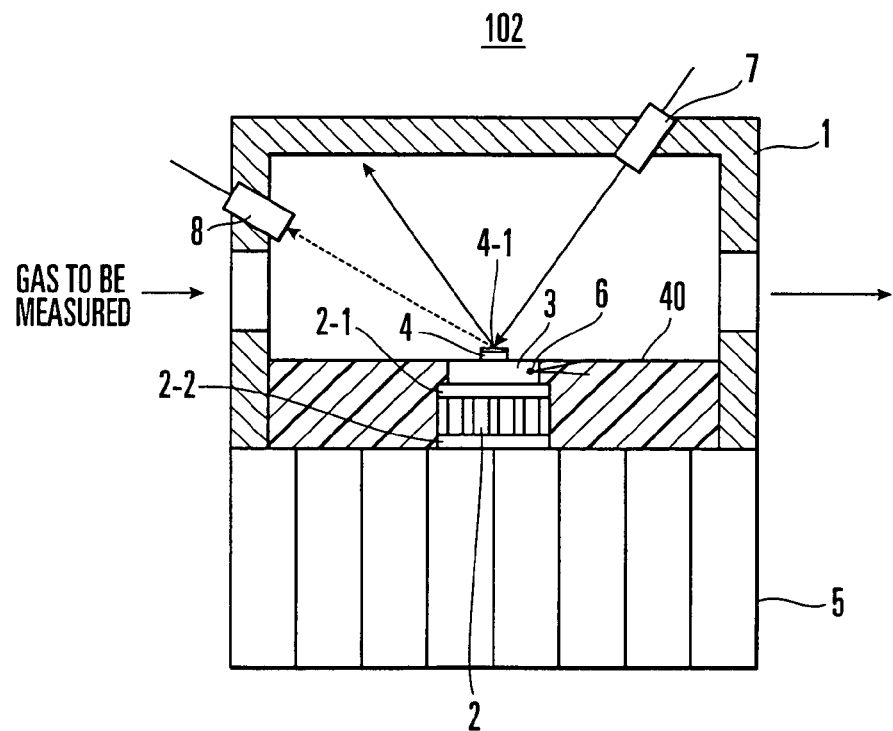
FIG. 16 is a view showing the main part of a conventional chilled mirror dew point hygrometer using the scattered light detection scheme.
Figure 17:
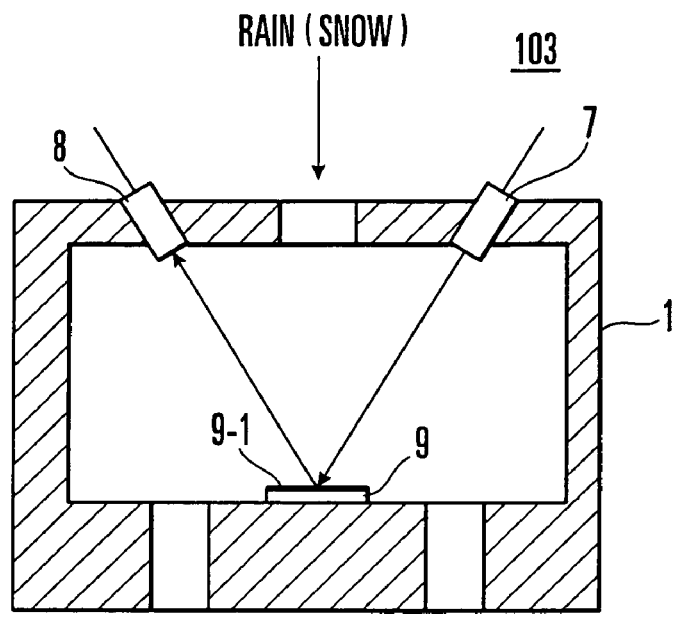
FIG. 17 is a view showing the main part of a conventional weather meter using the specular reflection detection scheme.
Figure 18:
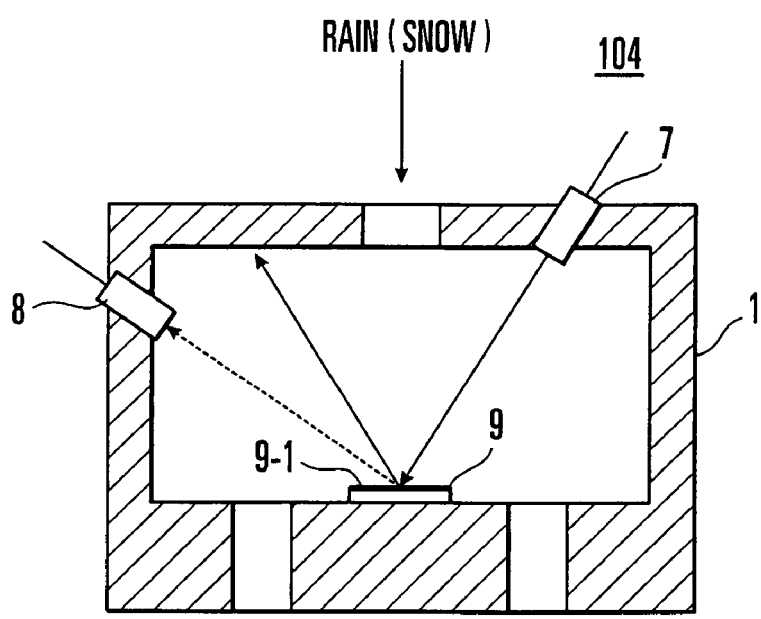
FIG. 18 is a view showing the main part of a conventional weather meter using the scattered light detection scheme.
Figure 19:
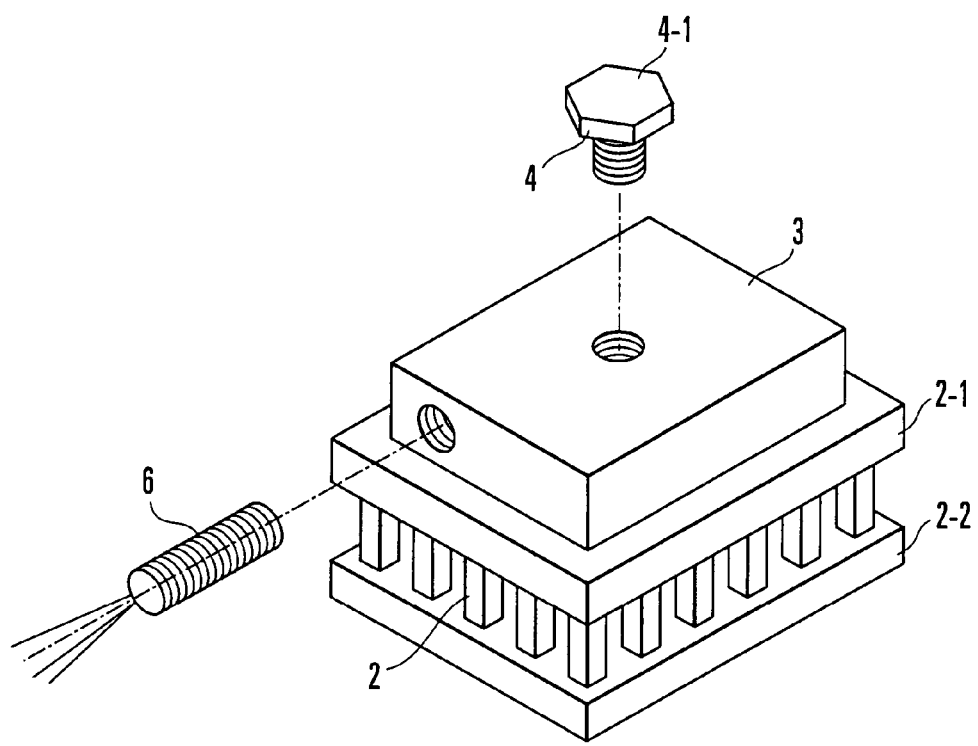
FIG. 19 is a perspective view showing a mounting structure for a mirror and temperature detection element in the conventional chilled mirror dew point hygrometer.

In the fifth embodiment as well, as shown in FIG. 14, providing a temperature detection element 22 at the joint surface between the heating surface 2-2 of the thermoelectric cooling element 2 and the heat sink 18 makes it possible to measure the temperature of the heat sink 18 with high accuracy and responsiveness. In addition, the cooling efficiency for the prism 19 can be improved by, for example, interrupting or limiting the current to the thermoelectric cooling element 2 when the temperature of the heat sink 18 reaches a certain temperature.

The first, second, and fifth embodiments described above are configured to detect dew condensation (moisture) which occurs on the detection surface 19-1. However, the same arrangement can detect frost formation (moisture) which occurs on the detection surface 19-1.

In addition, the first, second, and fifth embodiments described above use the thermoelectric cooling element (Peltier element) 2 as a cooling means for cooling the prism 19. However, they may use a helium refrigerator or the like.

In the first, second, and fifth embodiments, the heat sink 18 is joined to the heating surface 2-2 of the thermoelectric cooling element 2. However, the heat sink 18 need not always be provided.

Furthermore, the first to fifth embodiments described above use a triangular prism as the prism 19. However, these embodiments may use a trapezoidal prism obtained by cutting the bottom surface of a triangular prism, and may use prisms in various shapes.

Although the third and fourth embodiments are configured to detect rain which adheres to the detection surface 19-1, the same arrangement can detect snow which adheres to the detection surface 19-1.

INDUSTRIAL APPLICABILITY

The detector for detecting a state on the detection surface according to the present invention can be used as a dew condensation meter which detects dew condensation which occurs on the detection surface, a frosting meter which detects frost formation which occurs on the detection surface, a weather meter which detects rain which adheres to the detection surface, or a weather meter which detects snow which adheres to the detection surface.

The invention claimed is:

1. A detector for detecting a state on a detection surface, comprising:
    a prism which includes a first surface as a detection surface;
    light-emitting means for applying light to the detection surface through an interior of said prism;
    light-receiving means for receiving reflected light of light applied from said light-emitting means to the detection surface;
    state detection means for detecting a state on the detection surface on the basis of the reflected light received by said light-receiving means; and
    cooling means, provided on a second surface of said prism which serves as an exit surface of light to said light-receiving means, for cooling said prism,
    wherein said state detection means detects moisture produced on the detection surface of said prism which is cooled by said cooling means, on the basis of the specular reflection received by said light-receiving means.

2. A detector for detecting a state on a detection surface according to claim 1, further comprising a mirror on a third surface of the prism which reflects specular reflection of light applied from said light-emitting means to the detection surface and returns the light to the detection surface through the interior of said prism,
    wherein the second surface of said prism serves as an exit surface of light to said light-receiving means and an entrance surface of light from said light-emitting means, and
    the light that is returned by the mirror to the detection surface is then reflected by the detection surface and received by the light-receiving means.

3. A detector for detecting a state on a detection surface according to claim 2, wherein:
    said cooling means comprises a thermoelectric cooling element with one surface serving as a low-temperature-side surface and the other surface serving as a high-temperature-side surface,
    said thermoelectric cooling element is placed so as to make the low-temperature-side surface serve as the second surface side of said prism,
    a heat dissipation member is mounted on the high-temperature-side surface of said thermoelectric cooling element, and
    said light-emitting means and said light-receiving means are provided so as to extend through said thermoelectric cooling element and said heat dissipation member.

* * * * *